United States Patent [19]
Avellanet

[11] Patent Number: 5,613,948
[45] Date of Patent: Mar. 25, 1997

[54] ANNULAR PERFUSION BALLOON CATHETER

[75] Inventor: Ernesto Avellanet, Miami Lakes, Fla.

[73] Assignee: Cordis Corporation, Miami Lakes, Fla.

[21] Appl. No.: 643,255

[22] Filed: May 3, 1996

Related U.S. Application Data

[63] Continuation of Ser. No. 342,796, Nov. 21, 1994, abandoned, which is a continuation of Ser. No. 151,355, Nov. 12, 1993, abandoned.

[51] Int. Cl.$^6$ .................................................. A61M 29/00
[52] U.S. Cl. ................................................ 604/96; 606/194
[58] Field of Search ........................... 604/96, 101, 102; 606/192, 194

[56] References Cited

U.S. PATENT DOCUMENTS

| | | |
|---|---|---|
| 3,889,686 | 6/1975 | Duturbure . |
| 4,183,102 | 1/1980 | Guiset ................................ 604/101 X |
| 4,233,983 | 11/1980 | Rocco . |
| 4,423,725 | 1/1984 | Baran et al. . |
| 4,447,227 | 5/1984 | Kotsanis . |
| 4,581,017 | 4/1986 | Sahota . |
| 4,585,000 | 4/1986 | Hershenson . |
| 4,641,653 | 2/1987 | Rockey . |
| 4,694,827 | 9/1987 | Weiner et al. . |
| 4,723,549 | 2/1988 | Wholey et al. . |
| 4,762,130 | 6/1988 | Fogarty et al. . |
| 4,763,653 | 8/1988 | Rockey . |
| 4,771,777 | 9/1988 | Horzewski et al. . |
| 4,787,388 | 11/1988 | Hofmann . |
| 4,790,315 | 12/1988 | Mueller, Jr. et al. . |
| 4,795,427 | 1/1989 | Helzel . |
| 4,820,271 | 4/1989 | Deutsch . |
| 4,832,028 | 5/1989 | Patel . |
| 4,857,054 | 8/1989 | Helfer . |
| 4,877,031 | 10/1989 | Conway et al. . |
| 4,878,495 | 11/1989 | Grayzel . |
| 4,892,519 | 1/1990 | Sponger et al. . |
| 4,909,252 | 3/1990 | Goldberger ........................ 606/194 |
| 4,983,167 | 1/1991 | Sahota . |
| 5,000,734 | 3/1991 | Boussignac et al. . |
| 5,000,743 | 3/1991 | Patel . |
| 5,002,531 | 3/1991 | Bonzel ................................ 604/96 |
| 5,006,119 | 4/1991 | Acker et al. . |
| 5,019,042 | 5/1991 | Sahota . |
| 5,035,694 | 7/1991 | Kasprzyk et al. . |
| 5,046,503 | 9/1991 | Schneiderman . |
| 5,078,685 | 1/1992 | Colliver ............................. 604/96 |
| 5,087,247 | 2/1992 | Horn et al. . |
| 5,090,958 | 2/1992 | Sahota . |
| 5,090,960 | 2/1992 | Michael . |
| 5,108,370 | 4/1992 | Walinesky ......................... 604/96 |
| 5,129,883 | 7/1992 | Black . |
| 5,135,474 | 8/1992 | Swan et al. . |
| 5,137,513 | 8/1992 | McInnes et al. . |
| 5,147,377 | 9/1992 | Sahota . |
| 5,152,277 | 10/1992 | Honda et al. . |
| 5,160,321 | 11/1992 | Sahota . |
| 5,181,911 | 1/1993 | Shturman . |
| 5,195,955 | 3/1993 | Michael . |
| 5,195,971 | 3/1993 | Sirhan . |
| 5,205,822 | 4/1993 | Johnson et al. ................... 604/96 |
| 5,222,941 | 6/1993 | Michael . |
| 5,226,888 | 7/1993 | Arney . |
| 5,232,446 | 8/1993 | Arney . |
| 5,261,879 | 11/1993 | Brill . |
| 5,330,528 | 7/1994 | Lazim ................................ 623/1 |
| 5,338,300 | 8/1994 | Cox .................................... 604/96 |

Primary Examiner—Corrine M. McDermott
Attorney, Agent, or Firm—Lockwood, Alex, Fitzgibbon & Cummings

[57] ABSTRACT

A catheter suitable for percutaneous transluminal coronary angioplasty procedures and the like is provided. The catheter includes an annular balloon having an exterior wall, an interior wall and an inner longitudinal passageway defined by the interior wall. An elongated flexible tube extends into an interior compartment formed between the exterior and interior walls to pass fluid therebetween and inflate and deflate the balloon between a collapsed condition and an expanded condition. When in its expanded condition, the balloon engages a body vessel wall for dilating the body vessel, while simultaneously permitting perfusion of blood through the longitudinal passageway without need for an additional mechanism for pumping or channeling the blood.

6 Claims, 1 Drawing Sheet

1

ANNULAR PERFUSION BALLOON CATHETER

This application is a continuation of application Ser. No. 08/342,796, filed Nov. 21, 1994, now abandoned which is a continuation of application Ser. No. 08/151,355 filed Nov. 12, 1993, now abandoned.

The present invention relates generally to dilation catheters suitable for percutaneous transluminal coronary angioplasty procedures (PTCA), and more particularly to dilation catheters for use in PTCA procedures wherein blood is perfused distally of the dilation balloon during the inflation cycle of the balloon.

BACKGROUND AND SUMMARY OF THE INVENTION

PTCA procedures generally include inflation of a balloon in an arterial passage in an effort to clear a flow path for blood by dilating the stenosis. Inflation of the balloon and subsequent deflation and removal of the balloon results in treatment of the stenosis to increase the available cross-sectional area for blood to flow through the arterial passage.

In typical PTCA procedures, a guiding catheter is inserted into the cardiovascular system through the Tee-brachial or femoral arteries, generally under local anesthesia, until the distal tip of the catheter is in a coronary artery and generally positioned adjacent a stenosis. An extensible balloon of a dilation catheter is advanced through the guiding catheter alone or over a previously introduced guidewire until the balloon is positioned across the stenosis. The balloon is then inflated to a predetermined size with a fluid, preferably a radiopaque liquid, to radially compress the inside of the artery wall, thereby dilating the lumen of the artery. The balloon is then deflated so that the dilation catheter can be removed, and blood flow resumed through the dilated artery that now has a larger cross-sectional area to permit a greater volume of blood to flow therethrough.

In typical PTCA procedures, when the balloon of a dilation catheter is inflated in a coronary artery, all flow ceases through the coronary artery. If blood flow ceases for too long a period of time, the part of the heart which that coronary artery serves can begin to suffer from lack of blood, or ischemia. If the balloon remains inflated in the artery for prolonged periods of time, the injury caused by the absence of blood flow can be irreversible in some cases. On the other hand, it has been found that the probability of an artery wall or the stenosis maintaining its dilated cross-sectional area after having been subjected to dilation from an extensible balloon is directly related to the length of time that the balloon is inflated while located across the stenosis. However, the aforementioned potential problems associated with blocking blood flow are increased the longer the balloon is inflated in the artery.

Attempts have been made to produce dilation catheters that perfuse blood through a catheter or balloon when the balloon is inflated to avoid ischemia conditions distally of the balloon. For example, Wejay, et al., U.S. Pat. No. 5,158,540, disclose a perfusion catheter that perfuses blood during the balloon's inflation cycle to allow for longer inflation periods; however, the catheter is extremely complicated structurally and expensive to manufacture.

It is, therefore a general object of the present invention, to provide a new and improved perfusion balloon dilation catheter suitable for PTCA procedures.

Another object of the invention is to provide a dilation catheter suitable for PTCA procedures wherein the catheter perfuses blood around the inflated balloon and permits prolonged inflation times for the balloon.

Yet another object of the present invention is to provide a dilation catheter of a relatively simple structure for use in PTCA procedures where blood is perfused distally of the inflated balloon.

The present invention overcomes the problems associated with the prior art perfusion catheters by providing a perfusion balloon catheter having an annularly shaped extensible balloon including an exterior member and an interior member and an inner longitudinal passageway. The interior member and exterior member are sealingly connected along their edges to define an annular compartment. Also provided is an elongated flexible tubular member having a distal portion disposed in the annular compartment. A pathway is provided between the flexible tubular member and the annular compartment to radially expand the annular balloon so that the exterior member is capable of engaging a body vessel wall while blood is simultaneously perfused through the inner longitudinal passageway.

For a complete understanding of the present invention, reference is made to the embodiments illustrated in greater detail in the accompanying drawings and described by way of example. It should be understood that this invention is not limited to the particular embodiments illustrated herein, but is defined by the appended claims.

DETAILED DESCRIPTION OF THE PREFERRED EMBODIMENT

Figure 1:
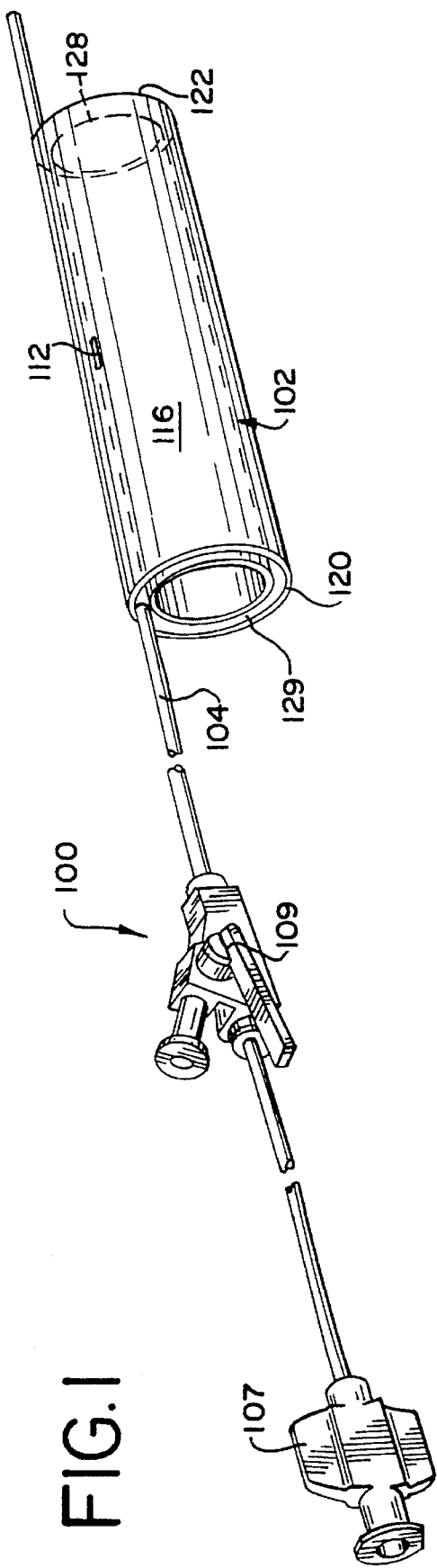
FIG. 1 is a perspective view of a balloon catheter made according to the present invention.

As illustrated in the drawings, the perfusion balloon catheter, generally designated at 100 in FIG. 1, made according to the present invention comprises an annularly shaped balloon member 102 located substantially near the distal end of elongated flexible tubular shaft 104. The illustrated catheter includes a Luer fitting 107 and a hub 109, both of a type well known in the art. Any suitable fitting and/or hub can be provided as desired.

Figure 2:
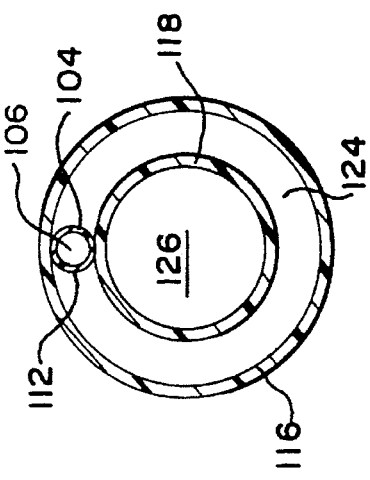
FIG. 2 is a cross-sectional view of FIG. 1.

As shown in FIG. 2, a lumen 106 is formed in tubular shaft 104 and may be of a substantially small diameter similar to that of the outer diameter of a standard guidewire preferably having a diameter of between about 0.008 inch and about 0.020 inch. Lumen 106 is utilized for carrying fluid, such as radiopaque saline solution or other fluid of a type well known in the art. The fluid carried by lumen 106 is communicated to balloon 102 for inflating and deflating balloon 102. The diameter of lumen 106 is large enough to carry sufficient amounts of fluid for inflating balloon 102.

Figure 3:
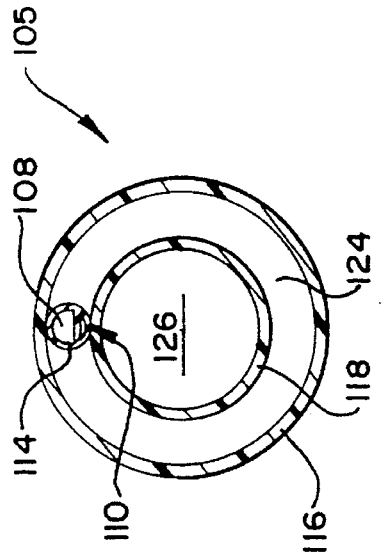
FIG. 3 is a cross-sectional view of an alternative embodiment of a distal end portion of a catheter made according to the present invention illustrating the dual lumen features.

An alternate embodiment of the catheter structure is shown in FIG. 3 and illustrates a dual lumen catheter 105, including lumen 108 and lumen 110. As illustrated, lumen 108 is substantially larger in cross-sectional area than lumen 110 and may be utilized to carry fluid to and from balloon 102 similarly to that of lumen 106. Lumen 110 may be utilized to receive a guidewire to provide assistance in placing the dilation catheter at the appropriate position in a body vessel.

Flexible tubing 104 utilized in the present invention is preferably formed of a suitable thermoplastic material, such as polyethylene, polyvinylchloride, and the like, or from a composite structure. Fluid is communicated to the interior of the balloon through openings, shown at 112 in FIGS. 1 and 2 at 114 in FIG. 3. It should be understood that other than being disposed in catheter 100 and catheter 105 respectively, openings 112 and 114 are identical. It is preferred that the openings 112 and 114 be slits that extend longitudinally with the flexible tube to prevent propagation of the openings while the tube 104 is being manipulated during insertion into a body vessel. Other shapes of openings, such as circular openings, may also be utilized. Although one opening between the flexible tube 104 and balloon 102 is preferred, more than one opening may be utilized to pass fluid between the flexible tube and the interior of the balloon.

The balloon 102 is annularly shaped and includes exterior wall member 116 and interior wall member 118. Exterior member 116 and interior member 118 are in seal-providing communication about their respective edges at 120 and 122 forming a cylindrically shaped balloon having spaced cylindrical walls defining an interior compartment 124 therebetween. Interior member or wall 118, defines an interior longitudinal passageway 126. Edges 120 and 122 can include radially extending end walls 128 and 129 which generally define the radial depth of the interior compartment 124.

Balloon 102 is an integral, fluid-tight structure that may be molded or otherwise formed as a single piece or it may be assembled from initially separate members such as the walls 116 and 118 and, when provided, end walls 128, 129. Each balloon may be produced from material well known in the art, such as, irradiated polyethylene, polyethylene terephthalate, nylon, polyamide, or other suitable flexible but relatively inelastic material. It should be noted that other than the inclusion of a dual lumen flexible tube in catheter 105, catheters 105 and 100 are structurally the same, and corresponding elements are identified with the same reference numerals.

The flexible tubular shaft 104 extends through the interior compartment 124 of balloon 102. This allows the flexible tube to pass fluid into the interior compartment 124 through opening 112. It should be understood that the lumen carrying fluid through the flexible tube 104 does not extend through the distal end of the tube 104; otherwise fluid would exit the tube into the body vessel and not be forced through opening 112 into the interior compartment 124. When balloon 102 is inflated to its expanded condition by the introduction of fluid into interior compartment 124, the exterior member 116 expands radially outwardly from longitudinal passageway 126. When fluid is removed from the interior compartment, exterior member 116 is substantially adjacent interior member 118 and the balloon 102 is in a substantially collapsed condition.

In a typical operation, catheter 100, 105 is generally advanced from the femoral artery or the Tee-brachial artery up the aortic root and is positioned in the appropriate coronary artery. Advancement of the catheter through an artery or body vessel is preferably performed when the balloon 102 is in its collapsed, non-inflated condition. The balloon 102 which is disposed at the distal end of the catheter is positioned across a restriction or stenosis in the artery. Thereafter, balloon 102 is inflated in the artery by pumping fluid through lumen 106 of flexible tubing 104. Inflation of the balloon causes the balloon, particularly exterior member 116, to radially expand causing exterior member 116 to engage the artery wall or stenosis and dilate the artery wall. Balloon 102 may remain in its expanded condition for a considerably longer time than conventional catheters because the blood is perfused past the balloon through longitudinal passageway 126 without need for a separate mechanism to pump or channel the blood.

When utilizing the catheter made according to the present invention, particularly the dual lumen catheter illustrated in FIG. 3, it may be desirable to initially insert a guidewire into the body vessel. The catheter may then be inserted over the guidewire wherein the guidewire extends through lumen 110 to assist in positioning the catheter in the body vessel. After the perfusion catheter has performed its function of dilating the restricted artery, the balloon 102 may be deflated and the catheter and guidewire, if utilized, removed.

It will thus be seen that the present invention provides a new and useful perfusion balloon catheter having a number of advantages and characteristics, including those pointed out herein and others which are inherent in the invention. Preferred embodiments of the invention have been described by way of example, and it is anticipated that modifications may be made to the described form without departing from the spirit of the invention or the scope of the appended claims.

We claim:

1. A dilation catheter for use in medical procedures comprising: an annular balloon member having an inner longitudinal passageway, an exterior cylindrical wall member and an interior cylindrical wall member, said exterior wall member and said interior wall member defining an annular cylindrical compartment therebetween, said inner longitudinal passageway being larger in radial extent than said annular compartment, said balloon member having a collapsed condition of a size allowing said catheter to be transported through a body vessel, and said balloon member having an expanded condition of a size allowing said balloon exterior wall member to engage a body vessel wall; an elongated flexible tubular member having a proximal end and a distal end, said tubular member having a longitudinal distal length sealingly disposed between said exterior cylindrical wall member and said interior cylindrical wall member and within said cylindrical annular compartment; said longitudinal distal length of the tubular member being fully enclosed within said balloon member annular cylindrical compartment in a manner such that said exterior and interior cylindrical balloon wall members are circular in cross-section along their respective lengths; means for passing fluid between said flexible tubular member and said annular compartment to vary said balloon member between said collapsed condition and said expanded condition; said exterior wall member expands radially outwardly from said inner longitudinal compartment when said balloon member is at its said expanded condition in order to cause said exterior wall member to dilate the body vessel wall; said exterior wall member and said interior wall member are substantially adjacent when said balloon member is in said collapsed condition; said exterior wall member is radially spaced from said interior wall member when said balloon member is in said expanded condition; and said balloon member is the only balloon member at said distal end of the dilatation catheter.

2. The dilation catheter of claim 1 wherein said means for passing fluid between said flexible tubular member and said annular compartment includes at least one pathway between said flexible tubular member and said annular compartment.

3. The dilation catheter of claim 1 wherein said flexible tubular member includes at least one longitudinal lumen therethrough.

4. The dilation catheter of claim 1 wherein said flexible tubular member includes a first lumen for transporting a fluid and a second lumen for transporting a guidewire.

5. The dilation catheter of claim 1, further including a radially extending end wall joining said exterior wall member and said interior wall member.

6. The dilation catheter of claim 1, further including two radially extending end walls joining respective longitudinal edges of said interior wall member and exterior wall member.

\* \* \* \* \*

UNITED STATES PATENT AND TRADEMARK OFFICE
CERTIFICATE OF CORRECTION

PATENT NO. : 5,613,948
DATED : March 25, 1997
INVENTOR(S) : Ernesto Avellanet

It is certified that error appears in the above-indentified patent and that said Letters Patent is hereby corrected as shown below:

Item [56]
On the Cover Page, under "References Cited, U.S. PATENT
    DOCUMENTS", Patent No. 5,108,370, "Walinesky" should read
    --Walinsky--.
Col. 1, line 63, "therefore a" should read --therefore, a--;
    line 63, "invention, to" should read --invention to--.
Col. 3, line 6, "2 at 114" should read --2 and at 114--.

Signed and Sealed this

Twenty-fourth Day of March, 1998

Attest:

BRUCE LEHMAN

*Attesting Officer*     *Commissioner of Patents and Trademarks*